United States Patent
Hautvast et al.

(10) Patent No.: US 11,033,254 B2
(45) Date of Patent: Jun. 15, 2021

(54) IMAGE GUIDANCE SYSTEM

(71) Applicant: KONINKLIJKE PHILIPS N.V., Eindhoven (NL)

(72) Inventors: Guillaume Leopold Theodorus Frederik Hautvast, Veldhoven (NL); Jacek Lukasz Kustra, Nederland (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 463 days.

(21) Appl. No.: 15/735,398

(22) PCT Filed: Jun. 16, 2016

(86) PCT No.: PCT/EP2016/063812
§ 371 (c)(1),
(2) Date: Dec. 11, 2017

(87) PCT Pub. No.: WO2016/207048
PCT Pub. Date: Dec. 29, 2016

(65) Prior Publication Data
US 2018/0168559 A1 Jun. 21, 2018

(30) Foreign Application Priority Data
Jun. 26, 2015 (EP) .................................. 15174061

(51) Int. Cl.
*A61B 10/00* (2006.01)
*A61B 10/02* (2006.01)
(Continued)

(52) U.S. Cl.
CPC ...... *A61B 10/0241* (2013.01); *A61B 17/3403* (2013.01); *A61B 90/11* (2016.02);
(Continued)

(58) Field of Classification Search
CPC .................................................. A61B 10/0241
See application file for complete search history.

(56) References Cited

U.S. PATENT DOCUMENTS

| 5,398,690 A | 3/1995 | Batten et al. |
| 6,423,009 B1 | 7/2002 | Downey et al. |

(Continued)

FOREIGN PATENT DOCUMENTS

WO WO9823214 A1 6/1998

*Primary Examiner* — Joseph M Santos Rodriguez
(74) *Attorney, Agent, or Firm* — Sherry Austin

(57) ABSTRACT

It is an object of the invention to provide for a system that can be used to improve a cancer related clinical workflow compared to the current cancer related clinical workflow. This object is achieved by an image guided system configured for supporting a combined biopsy and treatment procedure using image guidance to bring a needle from a defined location to a predetermined end location in a subject of interest. The image guidance system comprises a medical imaging system (580) configured for acquisition of medical images of a region of interest (403) in the subject of interest, wherein the medical images are used to determine a current position of the predetermined end location (404). The image guidance system further comprises needle guidance system (402, 403) configured for defining a needle position in space and thereby defining the defined location (405, 406) and configured for guiding a biopsy and treatment needle into the region of interest. The image guidance system also comprises a user interface system (530) configured for supporting both the biopsy and treatment procedure, such that a patient setup needs to be executed only once. The user interface system (530) comprises a calibration unit (540) for aligning the needle guidance system (402, 403) with the medical images.

22 Claims, 4 Drawing Sheets

(51) Int. Cl.
*A61B 17/34* (2006.01)
*A61B 90/11* (2016.01)
*A61B 34/10* (2016.01)
*A61B 90/00* (2016.01)
*A61B 34/20* (2016.01)

(52) U.S. Cl.
CPC .......... *A61B 2017/3411* (2013.01); *A61B 2017/3413* (2013.01); *A61B 2034/107* (2016.02); *A61B 2034/2051* (2016.02); *A61B 2090/3782* (2016.02)

(56) References Cited

U.S. PATENT DOCUMENTS

| | | | |
|---|---|---|---|
| 6,824,516 B2 | 11/2004 | Batten et al. | |
| 8,123,698 B2 | 2/2012 | Mark | |
| 8,447,384 B2 | 5/2013 | Xu | |
| 8,812,080 B2 * | 8/2014 | Nachabe | G16H 40/63 600/424 |
| 2007/0123815 A1 | 5/2007 | Mark | |
| 2012/0071749 A1 * | 3/2012 | Xu | A61B 6/5247 600/411 |
| 2013/0317352 A1 * | 11/2013 | Case | A61B 8/0841 600/424 |

* cited by examiner

IMAGE GUIDANCE SYSTEM

CROSS-REFERENCE TO PRIOR APPLICATIONS

This application is the U.S. National Phase application under 35 U.S.C. § 371 of International Application Serial No. PCT/EP2016/063812, filed on Jun. 16, 2016, which claims the benefit of European Patent Application No. 15174061.0, filed on Jun. 26, 2015. This application is hereby incorporated by reference herein.

FIELD OF THE INVENTION

The invention relates to a system in the field of medical image guided interventions.

BACKGROUND OF THE INVENTION

Amongst others, diagnosis of cancer is performed based on tissue samples obtained in a biopsy procedure. These biopsy procedures are often performed systematically, taking a number of biopsy samples from a standardized set of locations inside the prostate. With the availability of fusion-guided biopsy systems, this is now shifting to a more targeted approach in which a suspicious lesion as shown on magnetic resonance imaging (MRI) is being sampled. If a patient has a biopsy proven tumor, this patient is often treated, e.g. by means of radiotherapy.

At present, altogether, a complete clinical flow from MRI, via fusion guided biopsy and pathology to treatment, typically takes 2-4 weeks in most hospitals. During this workflow first an MRI image may be acquired on which suspicious tissue may be identified. The MRI image could be used during an ultrasound guided biopsy procedure, by fusing it with the ultrasound images acquired by the ultrasound imaging system used for biopsy guidance. In this case the MRI image determines a predetermined end location in the subject of interest (e.g. the patient). At this predetermined end location a biopsy needs to be taken. Biopsy samples retrieved during the biopsy procedure are send to a pathology department, where the tissue is being analyzed for tumor presence and aggressiveness. This leads to a biopsy result describing a likelihood of tumor presence in a biopsy sample. If the patient has biopsy proven cancer, the patient will usually be treated. During treatment a whole organ can be treated. Alternatively, focal treatment is performed, wherein only part of the organ is being treated. Examples of possible treatments are e.g. brachytherapy, cryotherapy, thermal ablation treatment. A medical image, for example the MRI image can be used for treatment planning. This image determines the predetermined end location for treatment. This could for example be the location where a brachy seed or a needle needs to be positioned During this clinical workflow the patient needs to come to the hospital multiple times to undergo these procedures. These visits, as well as the multiple usage of hospital resources involve substantial cost.

WO2010/140075A2 discloses a method for integrating diagnosis and treatment for internal tissues, comprising: imaging at least a portion of an internal organ of a subject using a first technology capable of differentiating tissue types; targeting and accessing biopsy sites using images of the first technology fused with images of a second technology capable of real-time image updates; planning treatment of at least one of the biopsy sites using the images of the first technology; and guiding instruments for treating the at least one biopsy site by fusing the images of the first technology with the images of the second technology

SUMMARY OF THE INVENTION

It is an object of the invention to provide for a system that enables to improve a cancer related clinical workflow compared to the current cancer related clinical workflow. This object is achieved by an image guidance system configured for supporting a combined biopsy and treatment procedure using image guidance to bring a needle from a defined location to a predetermined end location in a subject of interest, wherein the image guidance system comprises
  a medical imaging system configured for acquisition of medical images of a region of interest in the subject of interest, wherein the medical images are used to determine a current position of the predetermined end location and
  a needle guidance system configured for defining a needle position in a space and thereby defining the defined location and configured for guiding a biopsy and treatment needle into the region of interest and
  a calibration unit for determination of calibration settings and thereby aligning the needle guidance system with the medical images prior to the biopsy and
  a user interface system configured for supporting both the biopsy and treatment procedure, such that a patient setup needs to be executed only once for both procedures;
wherein the image guidance system is further configured to automatically use the calibration settings determined prior to biopsy during treatment.

It is an insight of the inventors that current biopsy and treatment procedures comprise several similarities for example in the case of prostate cancer treatment. But also in the case of breast cancer. Both procedures induce similar trauma, thus requiring similar anaesthesia (and related devices) and antibiotics to prevent potential infections. Also, both procedures are performed in similar, clean environments in which the aforementioned medical devices are present. The availability of such clean operating rooms is limited.

Furthermore, both for biopsy and treatment, a patient setup needs to be executed. Executing a patient setup means preparing the patient and the system for the procedure. This means for example selecting the patient in the system, providing a name, date of birth to the system, positioning the patient (e.g. on the back for prostate cancer treatment). Executing this patient setup twice increases the time in the operation room and thereby increases the costs. Also, as part of executing the patient setup a calibration has to be performed to align a needle guidance system with medical images acquired with the medical imaging system. Needle guidance system should be understood as a system that could be used to guide a needle into the subject of interest. Examples of needle guidance systems are EM tracking means, optical shape sensing means, optical trackers or a grid and needle sleeves. Such grid is for example known from prostate brachytherapy.

Performing the calibration independently for the biopsy and treatment procedure does not only increase the total time spend on the procedures, it may also introduce errors as subsequential calibration procedures may produce (slightly) different results. Therefore, by means of the invention, the total time spend in the hospital may be reduced per patient. Also the invention may reduce errors introduced because a biopsy was not taken in the same coordinate system as in which the treatment was performed. Thereby, the invention supports an improved clinical workflow.

The image guidance system comprises a medical imaging system. This medical imaging system could for example be an ultrasound imaging system, CT, PET, SPECT, X-ray or an MRI system. This imaging system is used to determine a current position of the predetermined end location. For example due to internal movement in the patient the position of the predetermined end location could alter. The predetermined end location could be determined based on a image acquired prior to the combined biopsy and treatment procedure and translated to the coordinate system of the medical imaging system used during the combined biopsy and treatment procedure by means of image registration. Alternatively, the predetermined end location could be determined based on one or more of the medical images acquired during the combined biopsy and treatment procedure.

As explained above examples of needle guidance system are EM tracking means, optical shape sensing, optical trackers or a grid. This needle guidance system determines a defined location for the needle. For example in case of the grid, a selected orifice through which the needle is to be inserted, determines the defined location for the needle. In case of needle guidance system that is configured for tracking (e.g. EM tracking, optical tracking), a tracked position determines the defined location. A trajectory could be determined from the defined location to the predetermined end location. In case of tracking the defined location could be updated regularly.

According to embodiments of the invention, the image guidance system is further configured to store one or more biopsy locations and one or more treatment locations in a same coordinate space. This is advantageous for follow-up. Pathology results are considered as ground-truth. By storing the biopsy and treatment locations in the same coordinate space, it is possible to correlate tumor presence and characteristics to a treatment dose given.

According to further embodiments of the invention the image guidance system is configured to create a treatment plan, such that a trajectory used during biopsy can be reused during treatment. For example one can use an outer needle, which is first used to guide the biopsy needle to the predetermined end location and subsequently use the outer needle to position an afterloader (in case of high dose rate (HDR) brachy treatment). In this way the outer needle only needs to be positioned once. Hereby, total procedure time can be further reduced. Furthermore, the burden to the patient may be reduced by a reuse of the trajectory.

According to further embodiments of the invention the image guidance system further comprises a registration means configured for registering a planning image based on which the predetermined end location is determined with at least one of the medical images. The "planning image" is a well known concept in the field of cancer treatment. It is the image which is used to define a target tissue and one or more organs at risk. A clinician determines a dose (e.g. radiation, thermal) restriction for each of these regions. Based on this restriction and the planning image a treatment plan can be made. This treatment plan determines for example the predetermined end location, but could also determine other settings like for example dwell times, power used in an ablation system.

The treatment plan could also be created during the combined biopsy and treatment procedure. Hereby, optionally also the biopsy result could be used for the creation of the treatment plan. Also before a biopsy result is retrieved multiple treatment plans could be created, which are dependent on the biopsy outcome. In this way after the biopsy result is retrieved, the user can select the treatment plan that best matches the biopsy result. In this way, waiting time for biopsy sample analysis can be efficiently used. In the above described cases the ultrasound image could be used as planning image. The image guidance means could comprise delineation means, such that a user could delineate regions of interest, like the target and one or more organs at risk.

According to embodiments of the invention, the image guidance system is configured to generate a first and a second report about the combined biopsy and treatment procedure, wherein the first report comprises different information than the second report. These reports could be send to different stakeholders in the hospital. For example a report comprising information on the treatment dose, e.g. by means of dose volume histograms could be send to the radiotherapist. Another report e.g. comprising the location where the biopsy has been taken could be send to the pathologist. Automatic report generation and automatically sending it to different stakeholders is advantageous as it further improves the clinical workflow.

According to embodiments of the inventions, the biopsy needle is a photonic needle. By use of a photonic needle suspicious tissue could potentially be detected within the patient and thereby the need of tissue analysis at the pathology department may be circumvented.

These and other aspects of the invention will be apparent from and elucidated with reference to the embodiments described hereinafter.

DETAILED DESCRIPTION OF THE INVENTION

Figure 1:
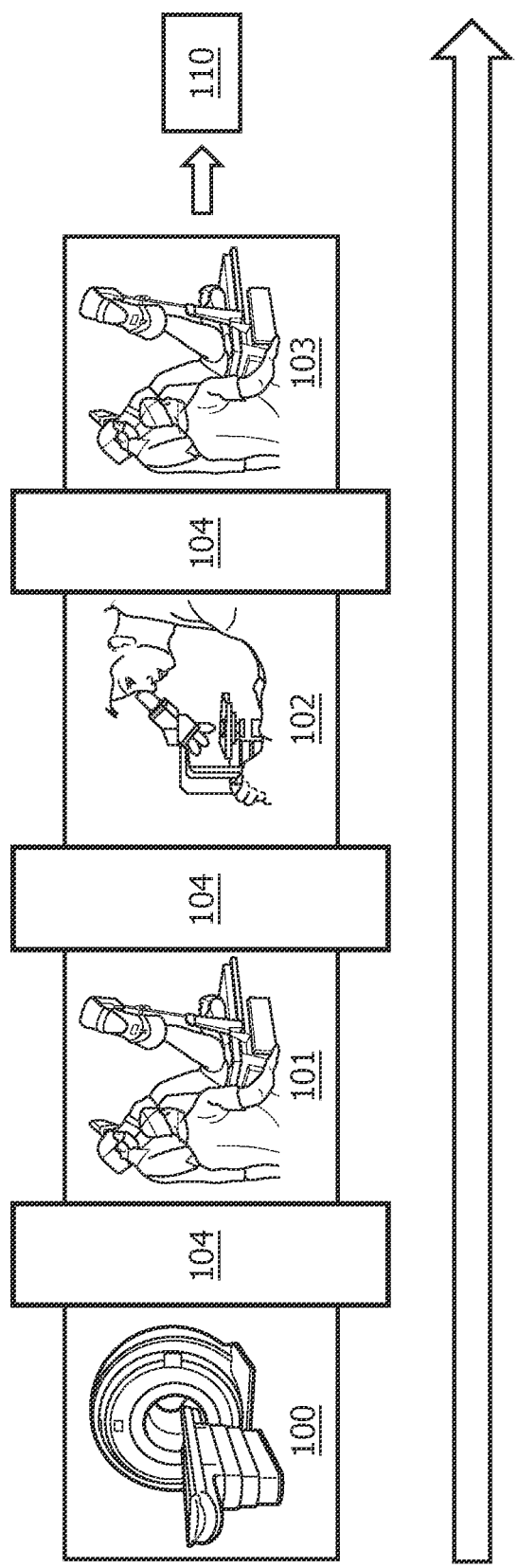
FIG. 1 shows an illustration of a clinical workflow which is known in the art and FIG. 2 shows an illustration of a clinical workflow wherein a biopsy and treatment procedure are combined and FIG. 3 shows an illustration of another clinical workflow wherein a biopsy and treatment procedure are combined and FIG. 4 shows an illustration of an image guidance system according to embodiments of the invention.

FIG. 1 shows an illustration of a clinical workflow which is known in the art. First a medical image is acquired 100 from the region of interest in the subject of interest. In this case the region of interest is a prostate. The acquired medical image is an MRI image. A physician determines regions (predetermined end locations) that are suspicious for comprising tumor tissue based on the MRI image. This will usually result in a delay of several days 104. After the delay 104 the patient has to come back to the hospital for the biopsy procedure 101. This biopsy could be performed under ultrasound guidance. The MRI image will be registered to the ultrasound image, such that that the predetermined end locations can be translated to a coordinate system of the ultrasound imaging system. A biopsy will be taken from these predetermined end locations. Then the patient will be send back home. The biopsy samples will be send to a pathology department, which will cause a further delay 104 of a few days. At the pathology department the biopsy sample will be analyzed 102 and checked for tumor presence. If the pathology department confirms tumor presence, the patient is invited back to the hospital, which causes another delay 104. During this delay also the treatment is planned based on a planning image, which could for example be the MRI image acquired at 100. Based on the planning image, e.g. locations (predetermined end locations) for brachytherapy seeds could be determined. During the treatment procedure 103, which could be performed under ultrasound guidance the planning image is registered to the images acquired by means of the ultrasound imaging system. In this way the ultrasound images could be used to guide a needle to the predetermined end locations and radioactive seeds could be positioned at the correct location in the case of LDR brachytherapy. In the case of HDR brachytherapy or the catheters can be positioned correctly, such afterloader can drive the HDR source as planned. After treatment the patient needs to come back to the hospital at regular intervals for follow-up 110.

Figure 2:
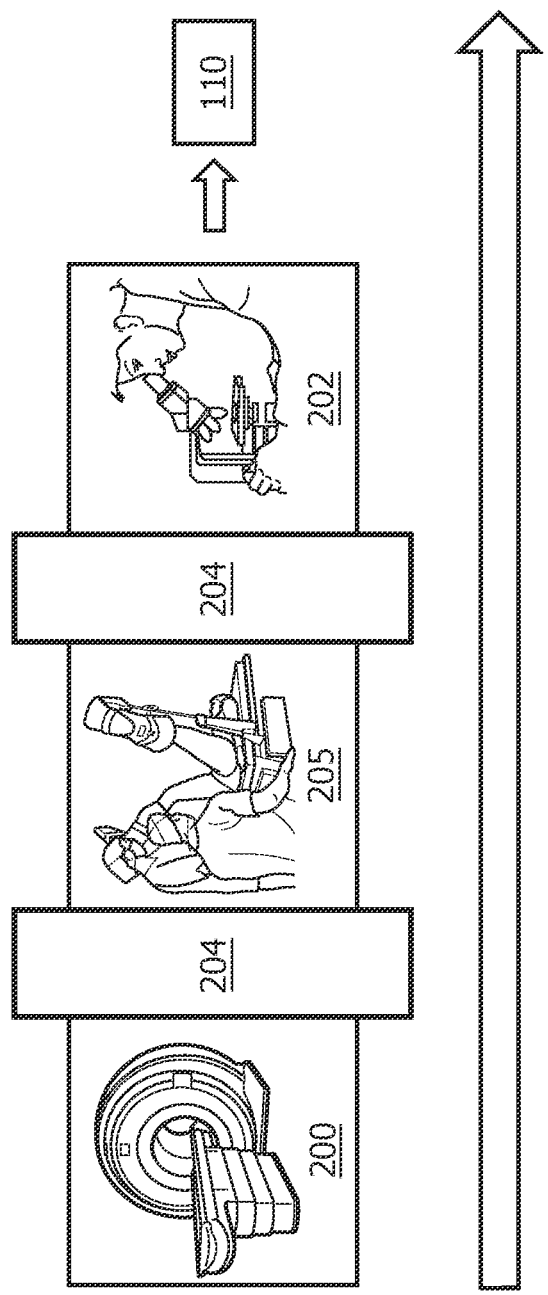

The invention is configured to support a combined biopsy and treatment procedure. FIG. 2 shows an illustration of a clinical workflow wherein a biopsy and treatment procedure are combined. This procedure again starts with the acquisition 200 of a planning image, based on which the predetermined end location can be determined. There could be a delay 204 between the acquisition of the planning image and the combined biopsy and treatment procedure. Alternatively, the planning image could be acquired with the same medical imaging system as used during the combined biopsy and treatment procedure. During the combined biopsy and treatment procedure first a patient setup is executed. A patient is being selected from the system and/or patient information is inserted into the system. The patient is positioned on the treatment table. In case of prostate cancer treatment the patient could be for example be positioned on his back, which is the position currently used for treatment. Also the patient could be positioned on his side, which is the position currently used for biopsy procedures. In the combined biopsy and treatment procedure preferably only one patient position is used. If the patient is positioned on the table a medical image is acquired and if necessary this image is registered with the planning image. Then the system is being calibrated. If one uses a grid to guide the needle into the patient, a stepper can be used to fix the distance between an ultrasound probe of the ultrasound imaging system and the grid. A needle can be inserted by a user into one of the orifices of the grid and be detected on a medical image acquired by means of the ultrasound imaging system. The calibration unit (FIG. 4, 540) is configured to transform a coordinate system of the grid to a coordinate system of the ultrasound imaging system based on this input. If a needle guidance system is a tracking means (like e.g. EM tracking or optical tracking), the needle could be brought to a certain position by a user. The calibration unit (FIG. 4, 540) is configured to link the coordinates indicating the needle's position provided by the tracking system to the coordinates indicating the needle's position provided by the ultrasound system. So the coordinate system of the tracking system could be transformed to the coordinate system of the ultrasound system (or other medical imaging system) based on the input provided by the user. The image guidance system is further configured to automatically use the calibration settings determined prior to biopsy during treatment. Therefore, calibration does not need to be redone, which decreases the risk for errors.

The introduction of focal treatment may reduce the incidence of treatment side effects. As a result, the total risk profile from biopsy and treatment in separate sessions, may be worse compared to the risk profile of a combined biopsy and treatment procedure, regardless of the outcome of pathology. This may be beneficial in indolent diseases, e.g. prostate cancer, if treatment of negative lesions results in little harm. In such circumstances, a suspicious lesion, as visible on MRI, can be biopsied and immediately treated 205. The biopsy samples can be analyzed after treatment 202. The resulting pathology results will be relevant to determine follow-up 110. As treating a lesion that is not yet confirmed to be malignant may seem radical, it is important to note that to date, many patients elect to undergo a radical prostatectomy to make sure the cancer is completely eliminated. A proven focal treatment should allow to provide similar guarantee, while potentially reducing treatment side effects.

Moreover, it is beneficial to store the location of biopsy samples and the treated regions in the information systems of the hospital, to facilitate efficient communication with the pathology department.

Figure 3:
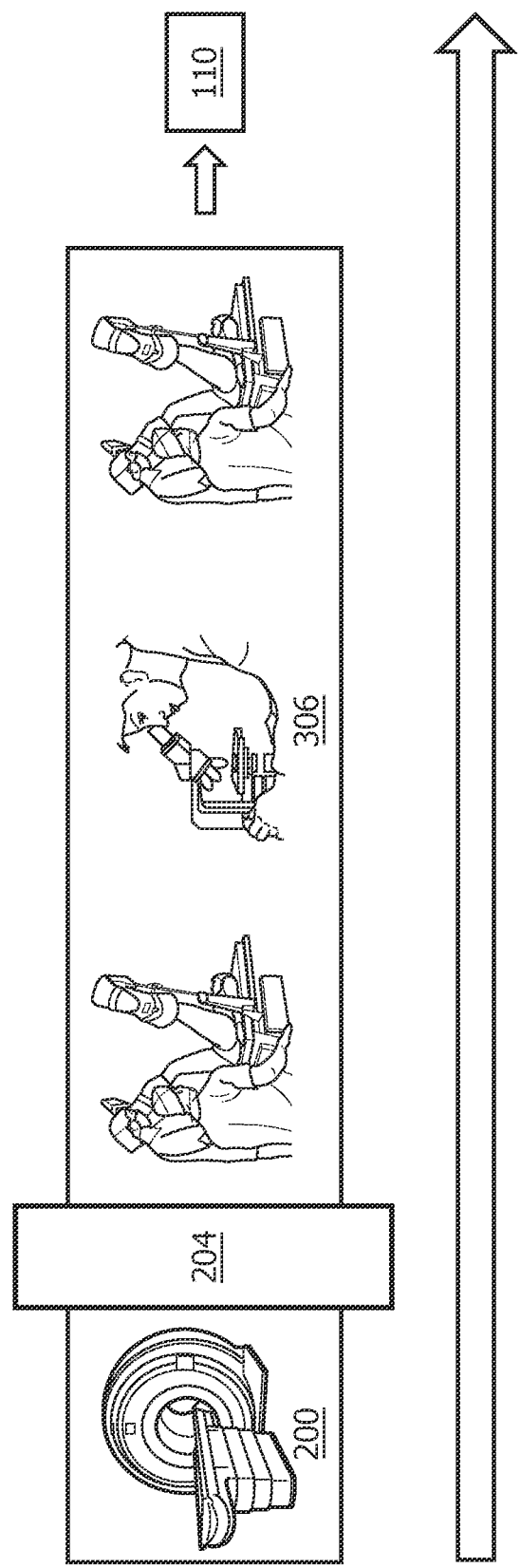

FIG. 3 shows an illustration of another clinical workflow wherein a biopsy and treatment procedure are combined 306. If pathology processing of the biopsy cores can indeed be accelerated such that it takes only limited time, e.g. less than 15 minutes, it may be economically viable to wait for the results while the patient is on the table in the operating room (as a second session for treatment may be much more expensive). Processing of the biopsy samples may be done inside the operating room 306 (using new point-of-care testing technologies), partially inside the operating room (digitizing pathology coupes in the operating room, to support remote analysis in the pathology department), or may be performed completely in the pathology department (requiring transport of the samples, aided by on-line communication means). Because the image guidance system is configured to automatically use the calibration settings determined prior to biopsy during therapy, calibration does not need to be redone, which decreases the risk for errors.

Alternatively, the use of a photonic needle to analyse tissue within the patient instead of analysis at the pathology department may further accelerate the procedure. In the context of this application a biopsy needle could therefore also be a photonic needle.

To improve time-efficiency, the interventional system could allow to start preparing a treatment assuming the pathology analysis confirms at least one of the biopsy samples comprising tumor tissue. These preparations may include creating different dose plans for the treatment, which are dependent on the biopsy outcome. Once the pathology results are available a subset of the dose plans is chosen for treatment delivery. Supporting this clinical workflow requires an image guidance system that enables both biopsy taking and treatment delivery in the suspicious lesion within a single session. In between the biopsy taking and treatment delivery, there will be time allocated to process the biopsy samples.

Moreover, it is beneficial to store the location of biopsy cores and the treated regions in the information systems of the hospital, to facilitate efficient communication with the pathology department.

Figure 4:
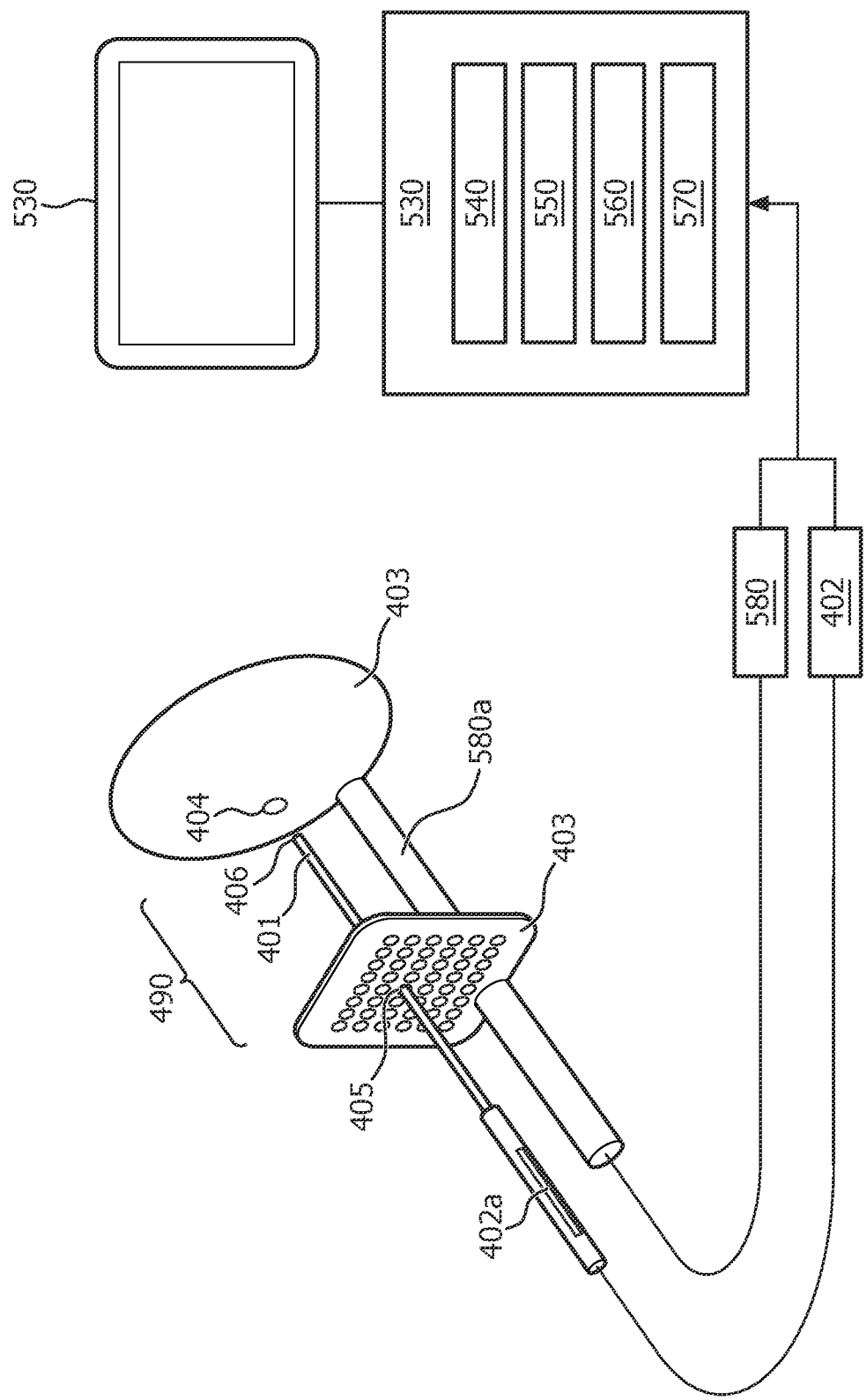

FIG. 4 shows an illustration of an image guidance system according to embodiments of the invention. The image guidance system comprises a medical imaging system 580 configured for acquisition of medical images of a region of interest 403 in the subject of interest. In this figure the medical imaging system is an ultrasound imaging system, comprising a transrectal probe 580a. The medical images are used to determine a current position of the predetermined end location 404. The image guidance system further comprises needle guidance system 402 and 403 configured for defining a needle position in space and thereby defining the defined location 405 and 406. The needle guidance system is further configured for guiding a biopsy and treatment needle into the region of interest. The needle guidance system comprises a grid 403 through which the biopsy and treatment needle can be inserted. The grid defines defined location 405, which could be considered a start location of the needle. If the length 490 of a part of the needle that is inserted through the grid is known, the grid can also be used to determine the defined location that is associated with tip of the needle 406. The system also comprises an electromagnetic (EM) tracking system 402, comprising a receiver 402a comprising receiver coils. Based on the position and orientation of the receiver coils within a electromagnetic field a position and orientation of the needle in space can be determined, in this way the defined location of the receiver coils of the needle can be determined. In this case of the length of the needle is known also the defined location of the needle tip 406 can be determined based on EM tracking system 402.

The image guidance system further comprises a user interface system 530 configured for supporting both the biopsy and treatment procedure, such that a patient setup needs to be executed only once. The user interface system comprises a calibration unit 540 for aligning the needle guidance system with the medical images. Examples of this calibration are explained above. The image guidance system further comprises registration means 550 configured to register the planning image with at at least one of the medical images acquired by the medical imaging system 510. The image guidance system further comprises delineation means 560 configured to delineate one or more regions of interest based on at least one of the medical images. The image guidance system also comprises treatment planning means 570 configured to create a treatment plan based on a biopsy result. This treatment planning means could for example take into account whether or not tumor tissue was found in a biopsy sample. Also the treatment planning means could be configured to calculate multiple treatment plans and the image guidance system could be configured to allow selection of one of these plans based on a biopsy result. In this way multiple treatment plans can be created prior to the biopsy result is retrieved. After a user has retrieved the biopsy result, he can select the treatment plan that best matches the biopsy result. This is likely the treatment plan which only results in a treatment dose in regions with containing biopsy proven cancer.

For both clinical workflows depicted in FIGS. 2 and 3 the image guidance system could be configured to create a treatment plan such that a trajectory used during biopsy can be reused during planning FIG. 4 shows an illustration of a reuse of the trajectory. An outer needle 401 is inserted into the patient such that it goes from the defined location 405 defined by the grid 402a to the predetermined end location 404 in a volume of interest 403 (target). In this illustration the trajectory is defined by the outer needle and is positioned between the defined location and the predetermined end location. A biopsy needle can be inserted in the outer needle to take a biopsy at the predetermined end location. In order to not unnecessarily further harm the patient, the trajectory defined by the outer needle is used by the image guidance system to calculate a treatment plan such that the trajectory can be reused for treatment. So the outer needle can be reused again to guide a treatment needle to the predetermined end location.

Whilst the invention has been illustrated and described in detail in the drawings and foregoing description, such illustrations and description are to be considered illustrative or exemplary and not restrictive; the invention is not limited to the disclosed embodiments.

The invention claimed is:

1. An image guidance system configured for supporting a combined biopsy and treatment procedure using image guidance to bring a needle from a defined location to a predetermined end location in a subject of interest, the image guidance system comprising:
 a medical imaging system configured for acquisition of medical images of a region of interest in the subject of interest, wherein the medical images are used to determine a current position of the predetermined end location;
 a needle guidance system configured for defining a needle position in a space and thereby defining the defined location, and configured for guiding the needle into the region of interest; and
 a user interface system configured for supporting the combined biopsy and treatment procedure, such that a patient setup needs to be executed only once for both the biopsy and the treatment in the combined biopsy and treatment procedure,
 wherein the image guidance system determines calibration setting for aligning the needle guidance system with the medical images prior to the biopsy, and
 wherein the image guidance system is further configured to automatically use, during the treatment, the calibration settings determined prior to the biopsy.

2. The image guidance system of claim 1, further configured to store position information for one or more biopsy locations and one or more treatment locations in a same coordinate space.

3. An image guidance system of claim 1, configured to create a treatment plan, such that a trajectory used during biopsy can be reused during treatment.

4. The image guidance system of claim 1, wherein the image guidance system is further configured for registering a planning image based on which the predetermined end location is determined with at least one of the medical images.

5. The image guidance system of claim 1, configured to generate a first report and a second report about the combined biopsy and treatment procedure, wherein the first report comprises different information than the second report.

6. The image guidance system of claim 1, wherein the image guidance system is further configured for enabling delineation of a region of interest.

7. The image guidance system of claim 1, wherein the image guidance system is further configured to create a treatment plan based on a biopsy result.

8. The image guidance system of claim 1, wherein the system is arranged to operate with a photonic needle as the biopsy needle.

9. The image guidance system of claim 1, configured to create multiple treatment plans and configured to allow a selection of one of the treatment plans based on a biopsy result.

10. The image guidance system of claim 5, wherein the first report is a biopsy report which includes first information pertaining to the biopsy, and wherein the second report is a treatment report which includes second information pertaining to the treatment.

11. The image guidance system of claim 10, wherein the first information identifies locations where the biopsy was taken, and wherein the second information includes at least one treatment dose volume histogram.

12. A method of supporting a combined biopsy and treatment procedure using image guidance to bring a needle from a defined location to a predetermined end location in a subject of interest, the method comprising:
   acquiring medical images of a region of interest in the subject of interest;
   determining a current position of the predetermined end location from the medical images;
   defining a needle position in a space and to define the defined location;
   guiding the needle into the region of interest;
   executing with a user interface system a patient setup only once for both the biopsy and the treatment in the combined biopsy and treatment procedure;
   determining calibration settings for aligning the needle guidance with the medical images prior to the biopsy; and
   automatically using, during the treatment, the calibration settings determined prior to the biopsy.

13. The method of claim 12, further comprising storing position information for one or more biopsy locations and one or more treatment locations in a same coordinate space.

14. The method of claim 12, further comprising creating a treatment plan, such that a trajectory used during biopsy can be reused during treatment.

15. The method of claim 12, further comprising registering a planning image based on which the predetermined end location is determined with at least one of the medical images.

16. The method of claim 12, further comprising generating a first report and a second report about the combined biopsy and treatment procedure, wherein the first report comprises different information than the second report.

17. The method of claim 12, further comprising delineating a region of interest.

18. The method of claim 12, further comprising creating a treatment plan based on a biopsy result.

19. The method of claim 12, further comprising operating with a photonic needle as the biopsy needle.

20. The method of claim 12, further comprising creating multiple treatment plans and allowing a selection of one of the treatment plans based on a biopsy result.

21. An image guidance system configured for supporting a combined biopsy and treatment procedure, the image guidance system comprising:
   a needle guidance system configured for defining a needle position in a space and thereby defining the defined location, and configured for guiding the needle into a region of interest indicated in a medical image; and
   a user interface system configured for supporting the combined biopsy and treatment procedure, such that a patient setup needs to be executed only once for both the biopsy and the treatment in the combined biopsy and treatment procedure,
   wherein the image guidance system determines calibration settings for aligning the needle guidance system with a medical image prior to the biopsy, and
   wherein the image guidance system is further configured to automatically use, during the treatment, the calibration settings determined prior to the biopsy.

22. A method of supporting a combined biopsy and treatment procedure using image guidance to bring a needle from a defined location to a predetermined end location in a subject of interest, the method comprising:
   determining a current position of the predetermined end location from a medical image;
   defining a needle position in a space and to define the defined location;
   executing with a user interface system a patient setup only once for both the biopsy and the treatment in the combined biopsy and treatment procedure;
   determining calibration settings for aligning a needle guidance with a medical image prior to the biopsy; and
   using, during the treatment, the calibration settings determined prior to the biopsy.

* * * * *